United States Patent [19]
Sallee et al.

[11] Patent Number: 5,449,349
[45] Date of Patent: Sep. 12, 1995

[54] INTRAVENOUS NEEDLE COVER/PROTECTOR

[76] Inventors: Wayne A. Sallee; Patricia L. Sallee, both of 310 Pebbleshire, Houston, Tex. 77062

[21] Appl. No.: 324,009

[22] Filed: Oct. 14, 1994

[51] Int. Cl.⁶ .......................................... A61M 25/02
[52] U.S. Cl. .......................... 604/180; 128/DIG. 6; 128/DIG. 26
[58] Field of Search .............. 604/174, 180; 128/888, 128/DIG. 6, DIG. 26

[56] References Cited

U.S. PATENT DOCUMENTS

| | | | |
|---|---|---|---|
| 3,194,235 | 7/1965 | Cooke | 604/180 |
| 3,782,377 | 1/1974 | Rychlik | 604/180 |
| 4,767,405 | 8/1988 | Lokken | 128/DIG. 26 |
| 5,074,847 | 12/1991 | Greenwell et al. | 604/174 |
| 5,112,313 | 5/1992 | Sallee | 604/180 |
| 5,116,324 | 5/1992 | Brierley et al. | 604/180 |
| 5,238,010 | 8/1993 | Grabenkort et al. | 128/888 |

Primary Examiner—Paul J. Hirsch
Attorney, Agent, or Firm—Mark A. Oathout

[57] ABSTRACT

The present invention relates to an improved I.V. cover/protector which includes a housing having a generally triangular top, a larger end-wall, a smaller end-wall, and two tapered sides. Two flexible wings are joined by a living hinge along the edge of the two tapered sides. An arch defines a passage through the larger end-wall into the housing. Protuberances are located along the inside walls of the arch for prehension of a catheter/catheter line. The passage defined by the arch and protuberances is oblique to the plane of the flexible wings so that the catheter/catheter line slants downwards toward the insertion site.

8 Claims, 3 Drawing Sheets

INTRAVENOUS NEEDLE COVER/PROTECTOR

BACKGROUND OF THE INVENTION

Applicant's previously obtained U.S. Pat. No. 5,112,313 for an I.V. cover/protector is incorporated herein by reference as a description of the problems associated with I.V. insertion sites, examples of catheters and needles and other general background information. Various problems associated with the invention described in U.S. Pat. No. 5,112,313 included inadequate retention and securement of the various catheter lines available on the market, and inadequate adaptability of the I.V. cover/protector.

SUMMARY OF THE INVENTION

The present invention relates to an improved I.V. cover/protector which includes a housing having a generally triangular top, a larger end-wall, a smaller end-wall, and two tapered sides. Two flexible wings are joined by a living hinge along the edge of the two tapered sides. An arch defines a passage through the larger end-wall into the housing. Protuberances are located along the inside walls of the arch for prehension of a catheter/catheter line. The passage defined by the arch and protuberances is oblique to the plane of the flexible wings so that the catheter/catheter line slants downwards toward the insertion site.

DETAILED DESCRIPTION

Figure 1:
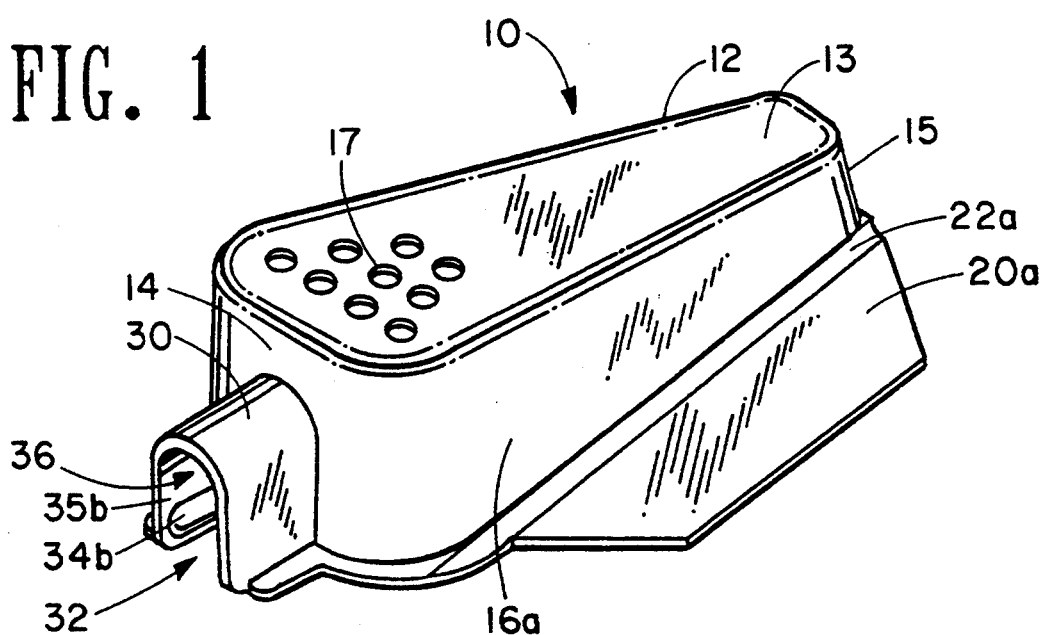
FIG. 1 is a perspective view of the invention.

Referring to FIGS. 1-5 an improved I.V. cover/protector 10 is shown. The I.V. cover/protector 10 is preferably transparent and generally includes a housing 12, flexible wings 20, and an arch 30.

The housing 12 includes a top 13, a larger end-wall 14, a smaller end-wall 15, and two sides 16a and 16b. Top 13 is generally triangular and includes ventilation holes 17. Side walls 16a and 16b are tapered downward from larger end-wall 14 to smaller end wall 15. The housing 12 defines an interior region 18 for the housing of the an I.V. needle, catheter 19, etc. The interior region is larger near larger end-wall 14 to accommodate a catheter 19, a butterfly attachment surface (not shown), etc. while the interior region near end-wall 15 is smaller to accommodate a needle and to more readily adapt to various extremities of a patient (not shown).

The smaller end-wall 15 includes a semi-circular opening or a tip radius cut 11. This opening inhibits pressure created by the I.V. cover/protector 10 upon a needle which extends beyond the smaller end-wall 15 or upon a vein into which the needle has been inserted.

Wings 20a and 20b are joined to sides 16a and 16b of the housing 12 by living hinges 22a and 22b, respectively. The bottom side of wings 20a and 20b lie in the same plane as the bottom side of the housing 12 to create a surface 24 for attaching the I.V. cover/protector 10 to the patient. The hinges 22a and 22b preferably comprise a notch or a strip of reduced thickness along the edge where the wings 20a and 20b meet sides 16a and 16b. The hinges 22 make the wings flexible and the I.V. cover/protector adaptable.

Figure 5:
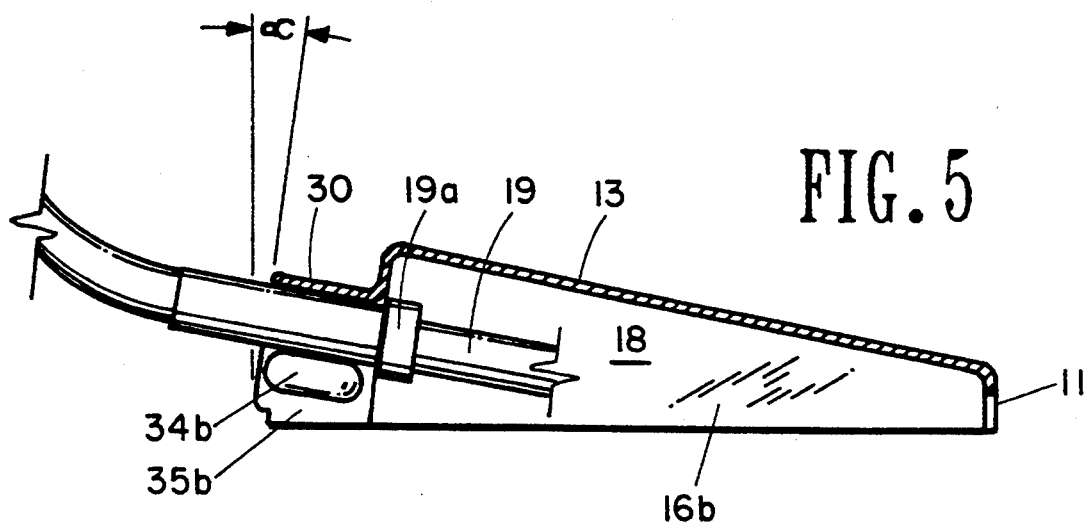
FIG. 5 is a cross sectional view taken along line 5—5 of FIG. 4 with a catheter/catheter line added to the view.

An arch 30 is joined to the larger end-wall 14 and defines a passage 32 into the housing 12. Two protuberances 34a and 34b are respectively joined to inside walls 35a and 35b of the arch 30. The arch 30 in conjunction with the protuberances 34a and 34b serves a prehensile function or as a clip for the catheter or pic line running to the insertion site; and defines a catheter/catheter line groove 36 in the portion of the passage 32 above the protuberances 34. The catheter/catheter line groove 36 has a radius designed to abut (but not squeeze so the catheter 19 can slide with respect to the housing 12 unless inhibited from sliding in one direction by a flange 19a on the catheter 19) the standard catheter/catheter lines 19 on the market. The arch 30 and the protuberances 34 are also angled such that the line groove 36 runs at an angle oblique to the plane which contains the wings 20a and 20b (and thereby oblique to the insertion site surface) so that the catheter 19 will be introduced and secured in the vein at a desirable angle. Preferably, the arch 30 extends 0.354 of an inch away from the larger end-wall 14, the span of the passage 32 inside the arch 30 is 0.218 of an inch, the radius of the line groove 36 is 0.109 of an inch, the span between the protuberances 34a and 34b is 0.166 of an inch, the angle $\alpha$ (shown in FIG. 5) from the vertical of the arch 30 and protuberances 34 (and thereby the line groove 36) is in the range of 6.5 to 8 degrees and is preferably 7.27 degrees; the long axis of the protuberances 34 as seen in FIG. 5 is 0.317 of an inch, the width of the protuberances 34 is 0.138 of an inch and the protuberances 34 are located between the top and the bottom of the arch 30.

The I.V. cover/protector 10 is preferably made of plastic such that wings 20a and 20b and arch 30 or flexible. With respect to the wings 20 the plastic along with hinges 22 promote maximum flexibility without reducing the retention strength of attachment tape or pads (not shown) allowing the cover/protector 10 to conform and hold to various limb dimensions and application sites and allowing improved checking of the application site. With respect to the arch 30 in conjunction with protuberances 34a, 34b the flexibility enhances the clip-like or prehensile function of the arch with respect to a catheter 19 or I.V. line.

Figure 6:
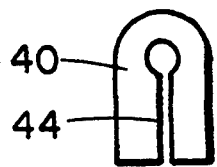
FIG. 6 is an elevational view of an insert which can be used in the invention.
Figure 7:
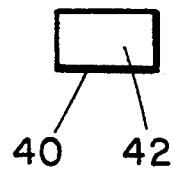
FIG. 7 is a top view of the insert shown in FIG. 6.
Figure 2:
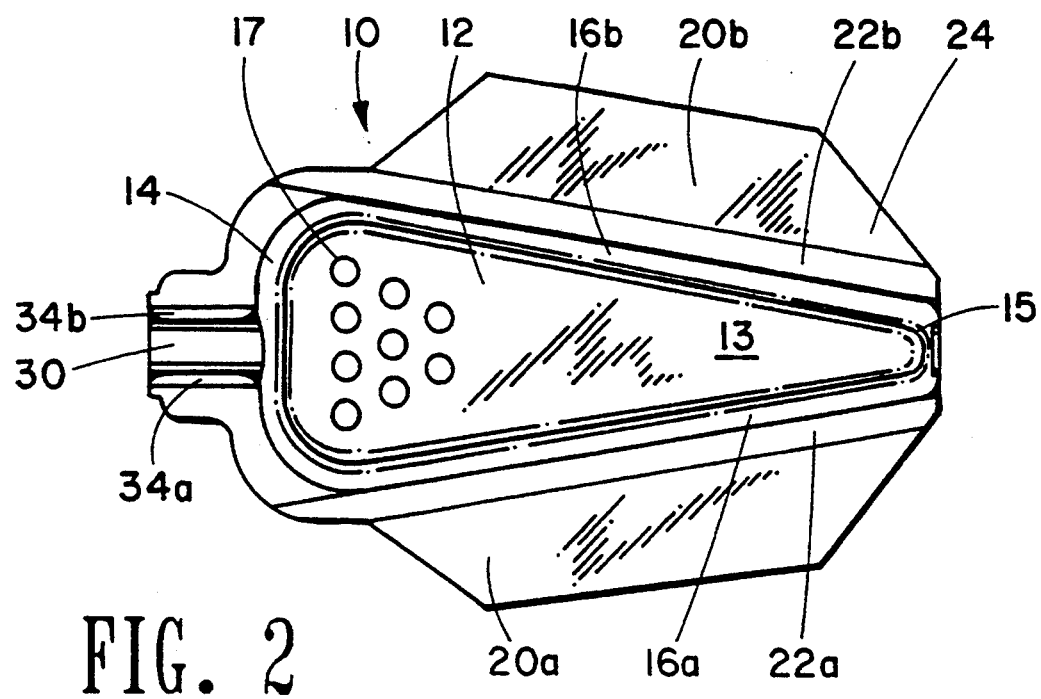
FIG. 2 is a bottom view of the invention.
Figure 3:
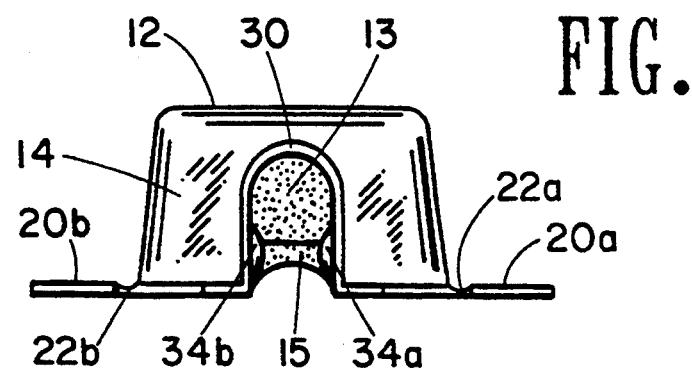
FIG. 3 is an elevational end view of the invention.
Figure 4:
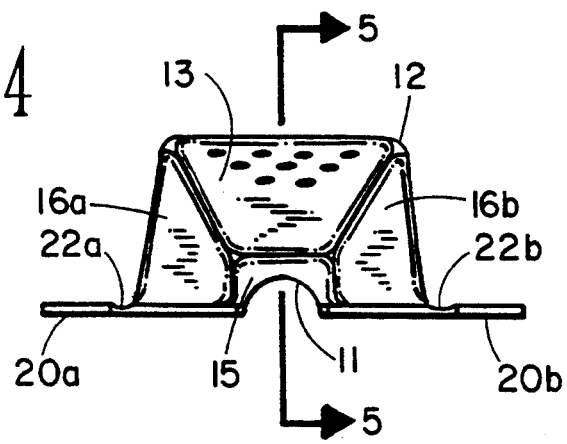
FIG. 4 is an elevational view from the other end of the invention.

In certain situations the catheter 19 or pic line may be too small to be retained by the arch 30. Referring to FIGS. 6 and 7 an insert 40 can be used as an adaptor in this situation. A preferable insert 40 is made of a foam material cut into an arch shape. The insert 40 is then mounted inside the arch 30 preferably with an adhesive applied to the surface 42 of the insert 40. The insert 40 has an opening or slit 44 for the insertion of the I.V. line or catheter 19. The insert 40 can be made of any other medically approved material such as a rubber, plastic, etc.; and the insert 40 can be made in other shapes such as a circle, a semicircle, etc.

The opening or passage 32 through larger end wall 14 is of a sufficient diameter to allow passage of the catheter/catheter line 19 but to prevent or inhibit withdrawal of the catheter/catheter line interface thereby serving as extra securement and as a retention means for keeping the catheter/needle 19 within the housing 12 and within the vein of the patient.

What is claimed is:

1. An improved I.V. cover/protector comprising:
   a housing;
   an arch extending from an end-wall of the housing and defining
   a passage into the housing; and
   two protuberances oppositely positioned inside of said arch.

2. The improved I.V. cover/protector according to claim 1 further including an insert mounted inside said arch, said insert having an opening.

3. The improved I.V. cover/protector according to claim 1 wherein said arch and said protuberances define a line groove angled oblique to a plane containing an attaching surface of the housing.

4. An improved I.V. cover/protector comprising:
   a housing having a triangular top, a larger end-wall, a smaller end-wall, and two tapered sides, wherein the housing defines an interior region;
   two hinges one each joined to each of the tapered sides;
   two wings, one each joined to each of the hinges, respectively;
   an arch extending from the larger end-wall defining a passage to the interior region of the housing;
   two protuberances oppositely positioned inside of said arch; and
   said arch and said protuberances defining a line groove angled oblique to said wings.

5. The improved I.V. cover/protector according to claim 4 wherein said hinges comprise a notch formed in said wings.

6. The improved I.V. cover/protector according to claim 4 wherein said smaller end-wall includes an opening.

7. The improved I.V. cover/protector according to claim 4 wherein said hinges comprise a strip of reduced thickness of said wings.

8. The improved I.V. cover/protector according to claim 4 further including an insert mounted inside said arch, said insert having an opening.

* * * * *